US00PP16993P3

(12) United States Plant Patent
Lim et al.

(10) Patent No.: US PP16,993 P3
(45) Date of Patent: Aug. 15, 2006

(54) SHRUB ROSE PLANT NAMED 'BAIING'

(50) Latin Name: *Rosa hybrida*
Varietal Denomination: BAIing

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 89 days.

(21) Appl. No.: 11/022,757

(22) Filed: Dec. 28, 2004

(65) Prior Publication Data

US 2006/0143745 P1 Jun. 29, 2006

(51) Int. Cl.
*A01H 5/00* (2006.01)

(52) U.S. Cl. ..... Plt./107

(58) Field of Classification Search ..... Plt./107, Plt./148, 149
See application file for complete search history.

*Primary Examiner*—Kent Bell
*Assistant Examiner*—June Hwu
(74) *Attorney, Agent, or Firm*—Buchanan Ingersoll PC

(57) ABSTRACT

A new and distinct variety of landscape shrub rose plant is provided which forms on a recurrent basis attractive large medium pink blossoms that assume a pale pink coloration with maturity. The plant exhibits a generally symmetrical vase-shaped growth habit, and can be used to form a distinctive low hedge. The attractive dark green glossy foliage contrasts nicely with the blossom coloration. High tolerance to Black Spot and Powdery Mildew is displayed. The plant can be grown to advantage to provide attractive ornamentation in parks and gardens.

2 Drawing Sheets

Botanical commercial classification: *Rosa hybrida*/Shrub Rose Plant.
Varietal denomination: cv. BAIing.

SUMMARY OF THE INVENTION

The new variety of *Rosa hybrida* landscape shrub rose plant was created at Yamhill, Oreg., U.S.A., during 1991 by artificial pollination wherein two parents were crossed which previously had been studied in the hope that they would contribute the desired characteristics. The female parent (i.e., the seed parent) was an unnamed and unreleased hybrid shrub rose plant from our breeding program designated 3901D (non-patented in the United States). The male parent (i.e., the pollen parent) was 'KORbin' variety (non-patented in the United States). The parentage of the new variety can be summarized as follows:

3901D×'KORbin'.

The seeds resulting from the above pollination were sown and plants were obtained which were physically and biologically different from each other. Selective study resulted in the identification of a single plant of the new variety having the distinctive ornamental characteristics hereafter described.

It was found that the new variety of the present invention:

(a) exhibits a generally symmetrical vase-shaped growth habit, (b) forms on a recurrent basis attractive large medium pink blossoms that assume a pale pink coloration with maturity, (c) forms dark green glossy foliage that contrasts nicely with the blossom coloration, (d) displays tolerance to Black Spot and Powdery Mildew; and (e) is particularly well suited for growing as attractive ornamentation in parks and gardens.

The young fuchsia-red buds open to vibrant medium pink blooms that fade to light pink creating an attractive blend of pink tints on the plant. The vase-shaped growth habit is well suited to form a low hedge that reaches a height of approximately 50 cm or can be present as a mixed planting in a perennial bed. The new variety is a hardy shrub that can be grown in U.S.D.A. Hardiness Zone Nos. 4 to 9.

The new variety well meets the needs of the horticultural industry. It can be grown to advantage where attractive ornamentation is desired, such as in parks and gardens.

The new variety can be readily distinguished from other varieties including its ancestors. More specifically, the parent designated 3901D forms light pink blossoms that are borne singly and light to medium green foliage, and the 'KORbin' parent is a Floribunda, forms pure white blossoms, and light green foliage.

The new variety also can be readily distinguished from the 'BUCbi' variety (U.S. Plant Pat. No. 4,225) and the 'AUSmary' variety (non-patented in the United States). The 'BUCbi' variety displays a taller growth habit, forms lighter green foliage, and commonly forms blossoms having a lesser number of petals. The 'AUSmary' variety displays a substantially taller growth habit, and forms cup-shaped blossoms having a substantially greater number of petals.

The new variety has been found to undergo asexual propagation by budding on an understock beginning in August 1992 and by the rooting of cuttings. 'Dr. Huey' rootstock was used during the budding. Such asexual propagation by these techniques at Yamhill, Oreg., U.S.A., St. Paul, Minn., U.S.A., and at Phoenix, Ariz., U.S.A., has shown that the characteristics of the new variety are stable and are strictly transmissible by such asexual propagation from one generation to another. Accordingly, the new variety reproduces true to type. The new variety grows well on its own roots.

Initially the new plant was designated 91H1, and was evaluated during 2002 and 2003 under the designation 02R306. The new variety subsequently has been named the 'BAling', and currently is being marketed while using the GARDEN ART and GRANDMA'S BLESSING trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn., U.S.A., and Yahmill, Oreg., U.S.A., during the 2003 and 2004 seasons.

DETAILED DESCRIPTION

Figure 1:
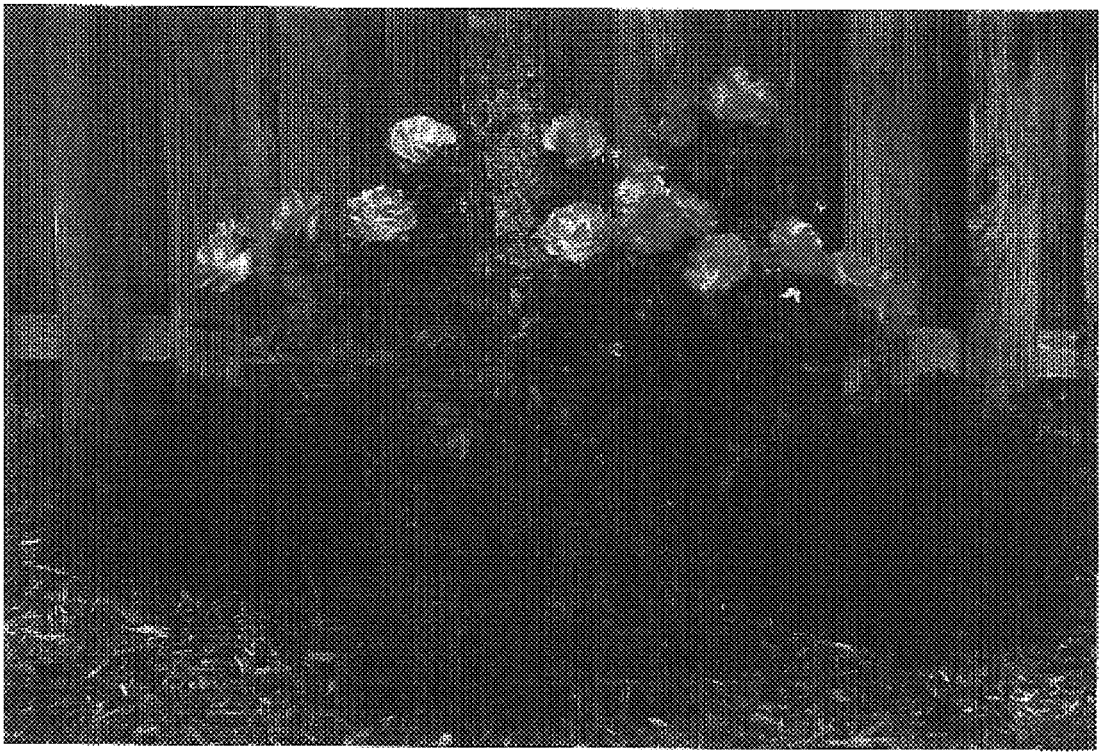
FIG. 1 illustrates a specimen of a typical flowering plant of the new variety which displays a generally symmetrical vase-shaped growth habit.
Figure 2:
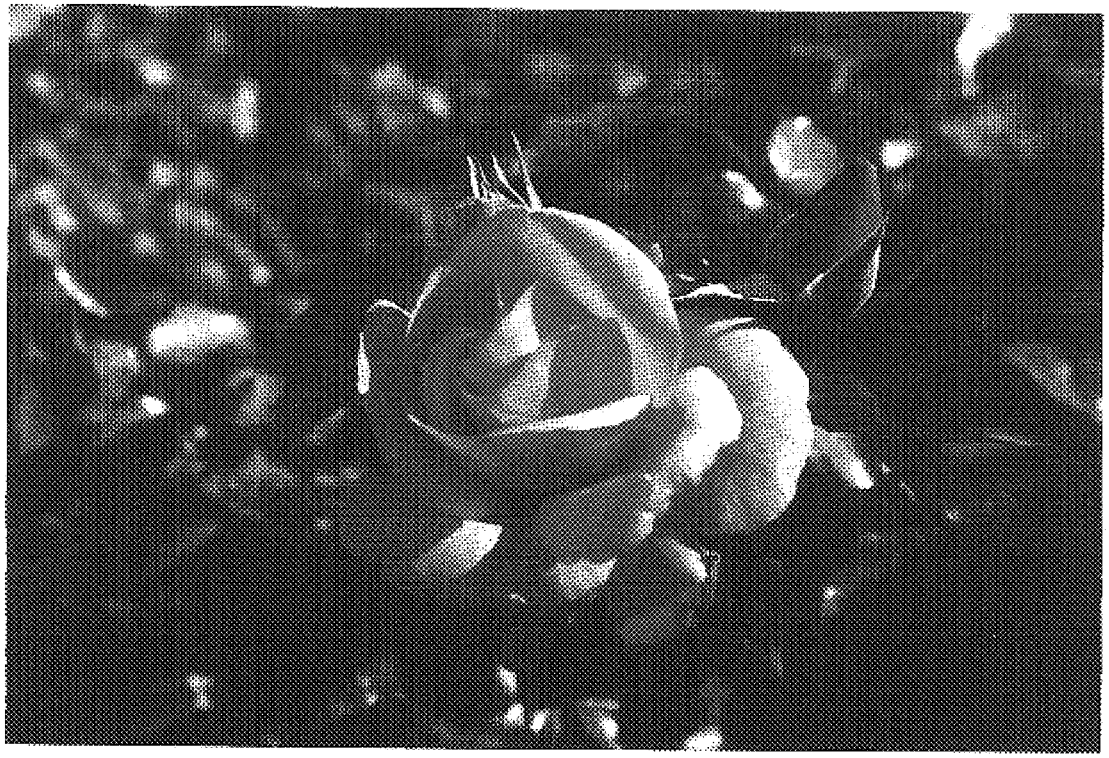
FIG. 2 illustrates a typical opening blossom and foliage of the new variety.
Figure 3:
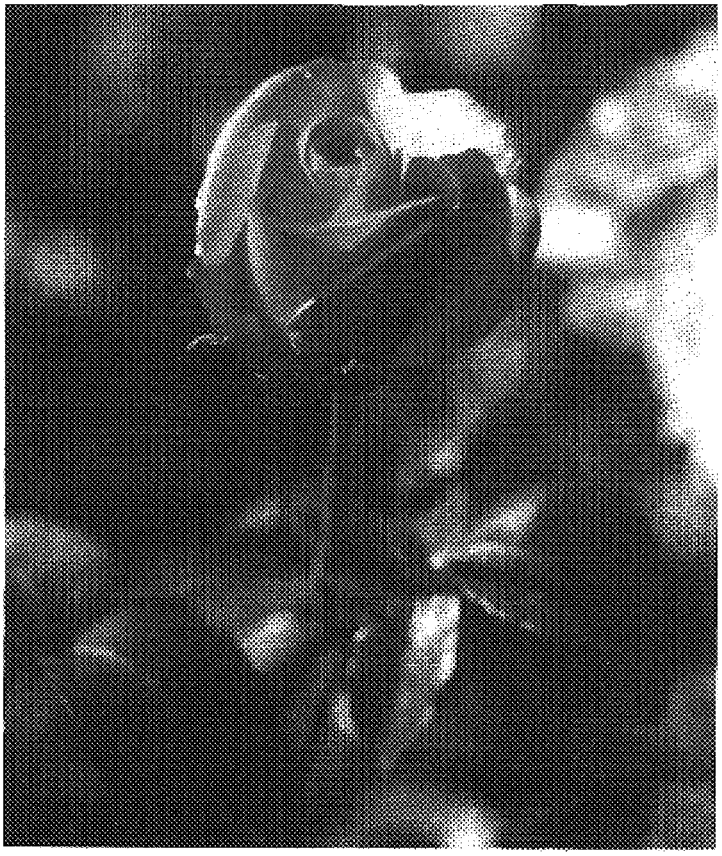
FIG. 3 illustrates a typical newly opened blossom and glossy dark green foliage of the new variety.
Figure 4:
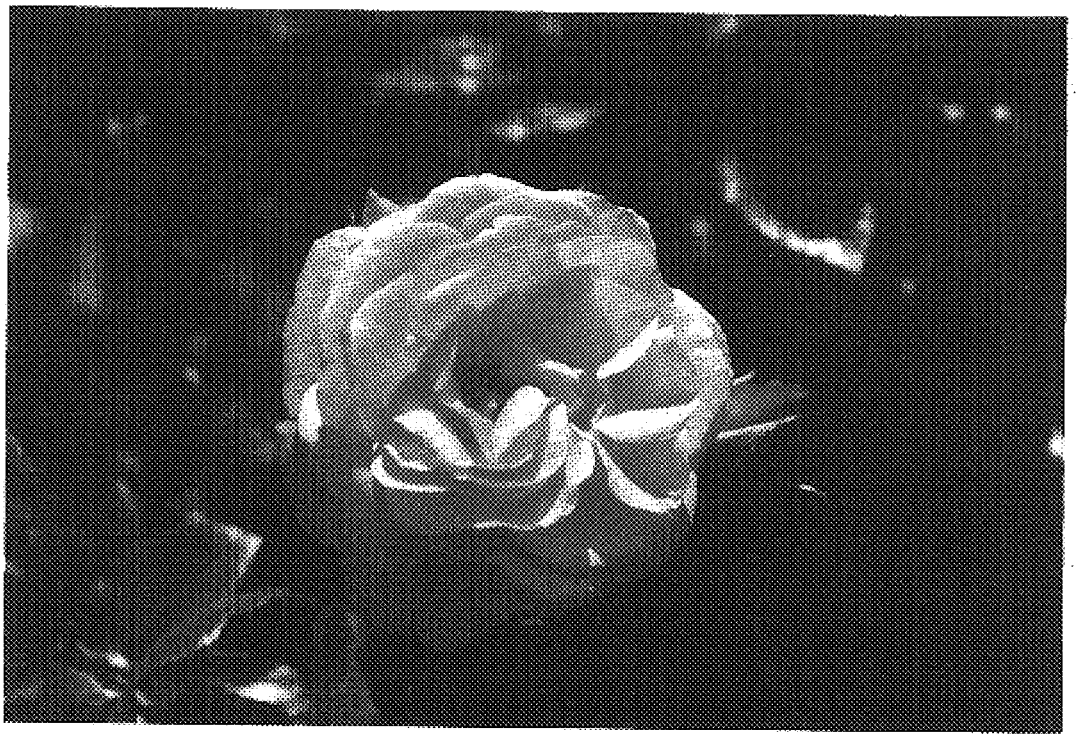
FIG. 4 illustrates a typical fully opened blossom of the new variety wherein the pink coloration has undergone some lightening.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June 2003 at Yamhill, Oreg., U.S.A., and July 2000 at St. Paul, Minn., U.S.A.

Botanical classification: *Rosa hybrida,* var. 'BAling'.
Class: Landscape Shrub.
Plant:
- *Height.*—Approximately 50 cm on average at the end of the growing season.
- *Width.*—Approximately 40 cm on average at the end of the growing season.
- *Habit.*—Generally symmetrical vase-shaped shrub in U.S.D.A. Hardiness Zone Nos. 4 to 9.

Branches:
- *Color.*—Young stems: Yellow-Green Group 144A suffused with Greyed-Purple Group 187B. Adult wood: Yellow-Green Group 146B with streaks of Grey-Brown Group 199A.
- *Texture.*—Young stems: glabrous. Adult wood: rough with bark-like ridges.
- *Thorns.*—Size: commonly approximately 6 mm in length on average. Shape: triangular to slightly hooked. Quantity: commonly approximately 4 on average per 5 cm branch length. Color: Red-Purple Group 59B.

Leaves:
- *Size.*—Commonly approximately 12.4 cm in length on average, and approximately 11.3 cm in width on average.
- *Stipules.*—Generally parallel with the auricle facing outward, approximately 1.4 cm in length on average, approximately 4.3 mm in width on average, and Greyed-Purple Group 183B in coloration with some Yellow-Green Group 146A to 146C on ridges.
- *Petioles.*—Upper surface: between Yellow-Green Group 146B and 146C with some Greyed-Purple Group 187B near the stipule. Under surface: Yellow-Green Group 146A and 146B. Length: approximately 2.6 cm on average. Diameter: approximately 1.8 mm on average. Texture: glabrous commonly with a few spines on both surfaces.
- *Leaflets.*—Number: 3, 5 (most often), and 7. Shape: ovate with a rounded base and an acuminate tip. Size: commonly approximately 6.7 cm in length on average, and approximately 3.6 cm in width on average. Margin: serrulate. Texture: bears a glossy finish. General appearance: dark green with a glossy upper surface when mature. Color (young foliage): Upper surface: Greyed-Purple Group 187C suffused with Greyed-Purple Group 185A and Yellow-Green Group 145B. Under surface: Greyed-Purple Group 187B suffused with Yellow-Green Group 146C near the main vein. Color (adult foliage): Upper surface: Yellow-Green Group 147A. Under surface: Yellow-Green Group 146A. Fall leaflet coloration: insignificant.

Inflorescence:
- *Number of flowers.*—Commonly approximately 5 blooms per lateral stem, and commonly in clusters.
- *Peduncle.*—Stiff, glabrous, commonly approximately 6.25 cm in length on average and near Green Group 143C tinted with Greyed-Purple Group 183C.
- *Sepals.*—Upper surface: Yellow-Green Group 144A with some streaking of Greyed-Red Group 182A and some pubescence. Under surface: Yellow-Green Group 144A blended with Greyed-Red Group 182A and with some pubescence. Size: approximately 2.5 cm in length on average. Shape: upright at bud stage, generally horizontal when opening, and reflexed at full bloom. Apex: initially apiculate, and then may assume a leaf shape with a main vein. Foliaceous appendages: commonly present on three outer sepals with one or two apendages per side that are approximately 6.5 mm in length on average with a pointed apex and a ciliate margin.
- *Buds.*—Shape: slender. Size: medium large. Length: approximately 3.0 cm on average. Diameter: approximately 1.8 cm on average. Color: Upper petal surface: Red-Purple Group 57C. Under petal surface: Red Group 46C suffused with Red-Purple Group 61B.
- *Flower.*—Shape: fully double. Diameter: approximately 9.0 cm on average. Color (when opening begins): Upper surface: between Red-Purple Group 57B and 57C. Under surface: between Red-Purple Group 57C and 57D. Color (when blooming): Upper surface: Red-Purple Group 66D blended with Red-Purple Group 68C and with Yellow-White Group 158D near the basal petal spot. Under surface: Red-Purple Group 66D and Red-Purple Group 67D with highlights of Red-Purple Group 67B and 67C. Color (at end of blooming): Upper surface: Red-Purple Group 68B and 68C and blended with White Group 155B near the basal petal spot. Under surface: between Red-Purple Group 66D and Red-Purple Group 68B. Color (basal petal spot): Yellow-White Group 158D. Fragrance: slight apple. Lasting quality: the blossoms commonly last approximately 5 to 7 days on average depending upon the temperature and sunlight exposure. Petal size: commonly approximately 4.5 cm in length on average, and approximately 4.8 cm in width on average. Petal number: commonly approximately 25 to 30 on average under normal growing conditions. Petal shape: orbicular. Petal texture: smooth and satiny. Petal drop: commonly the petals detach cleanly at full blossom maturity. Stamen: approximately 63 on average. Anthers: near Yellow Group 2B and 2C, approximately 2.9 mm in length on average, and approximately 1.1 mm in width on average. Filament length: approximately 1.2 cm on average. Filament color: Greyed-Orange Group 168D. Pistils: approximately 77 on average. Stigmas: Green-Yellow Group 1D blended with Red Group 43A near the styles, approximately 1.4 mm in length on average, and approximately 0.9 mm in width on average. Styles: Yellow Group 4D, and approximately 6.0 mm in length. Receptacle: generally urn-shaped, glabrous, and when the flower is fully open the height commonly is approximately 1 cm on average, the diameter commonly is approximately 9 mm on average, and the color is Yellow-Green Group 144A with Greyed-Purple Group 184A on the side exposed to the sun. Hips: glabrous, and Yellow-Green Group 144A and 144B suffused with Red Group 53A in coloration.

Development:

*Vegetation.*—Vigorous and strong.

*Blooming.*—Recurrent.

*Resistance to diseases.*—Highly tolerant to Black Spot and Powdery Mildew.

*Hardiness zone.*—U.S.D.A. Hardiness Zone Nos. 4 to 9.

We claim:

1. A new and distinct landscape shrub rose plant characterized by the following combination of characteristics:

(a) exhibits a generally symmetrical vase-shaped growth habit, (b) forms on a recurrent basis attractive large medium pink blossoms that assume a pale pink coloration with maturity, (c) forms dark green glossy foliage that contrasts nicely with the blossom coloration, (d) displays tolerance to Black Spot and Powdery Mildew; and (e) is particularly well suited for growing as attractive ornamentation in parks and gardens;

substantially as herein shown and described.

* * * * *